United States Patent [19]
Schmitt

[11] Patent Number: 6,036,362
[45] Date of Patent: Mar. 14, 2000

[54] RADIATION DIAPHRAGM WITH FILTER INDICATOR

[75] Inventor: Thomas Schmitt, Forchheim, Germany

[73] Assignee: Siemens Aktiengesellschaft, Munich, Germany

[21] Appl. No.: 09/102,608

[22] Filed: Jun. 23, 1998

[30] Foreign Application Priority Data

Jul. 9, 1997 [DE] Germany .......................... 197 29 414

[51] Int. Cl.[7] ...................................................... A61B 6/08
[52] U.S. Cl. ......................... 378/206; 378/150; 378/158
[58] Field of Search .................................. 378/206, 157, 378/158, 150, 156

[56] References Cited

U.S. PATENT DOCUMENTS

| | | | |
|---|---|---|---|
| 3,706,888 | 12/1972 | Wunsch | 378/157 |
| 3,982,825 | 9/1976 | Mitchell | 359/887 |
| 4,060,733 | 11/1977 | Franke et al. | 378/206 |
| 4,246,488 | 1/1981 | Hura | 378/206 |
| 4,400,827 | 8/1983 | Spears | 378/207 |
| 4,670,896 | 6/1987 | Klausz | 378/156 |
| 4,691,335 | 9/1987 | Telorack | 378/152 |
| 4,727,561 | 2/1988 | Fujisaki | 378/54 |
| 4,882,741 | 11/1989 | Brown | 378/152 |
| 4,933,960 | 6/1990 | Fujisaki | 378/53 |
| 5,081,660 | 1/1992 | Fujisaki | 378/156 |
| 5,136,627 | 8/1992 | Conrads et al. | 378/206 |
| 5,325,414 | 6/1994 | Tanaka et al. | 378/34 |
| 5,868,482 | 2/1999 | Edinger et al. | 353/84 |

FOREIGN PATENT DOCUMENTS 24 24 619   3/1979   Germany .

Primary Examiner—David P Porta
Assistant Examiner—Allen C Ho
Attorney, Agent, or Firm—Hill & Simpson

[57] ABSTRACT

A radiation diaphragm has an arrangement for introducing at least one radiation filter into the beam path of a radiation bundle emanating from a radiation transmitter. A light transmitter is provided for creating a light beam which optically represents the area of the radiation beam. A filter identifier is provided in the diaphragm housing for changing the color of the light beam dependent on whether a radiation filter is located in the radiation beam path. Based on the color of the light beam incident on the examination subject, it is possible to determine whether a radiation filter is located in the radiation beam path, and if so, which filter.

9 Claims, 1 Drawing Sheet

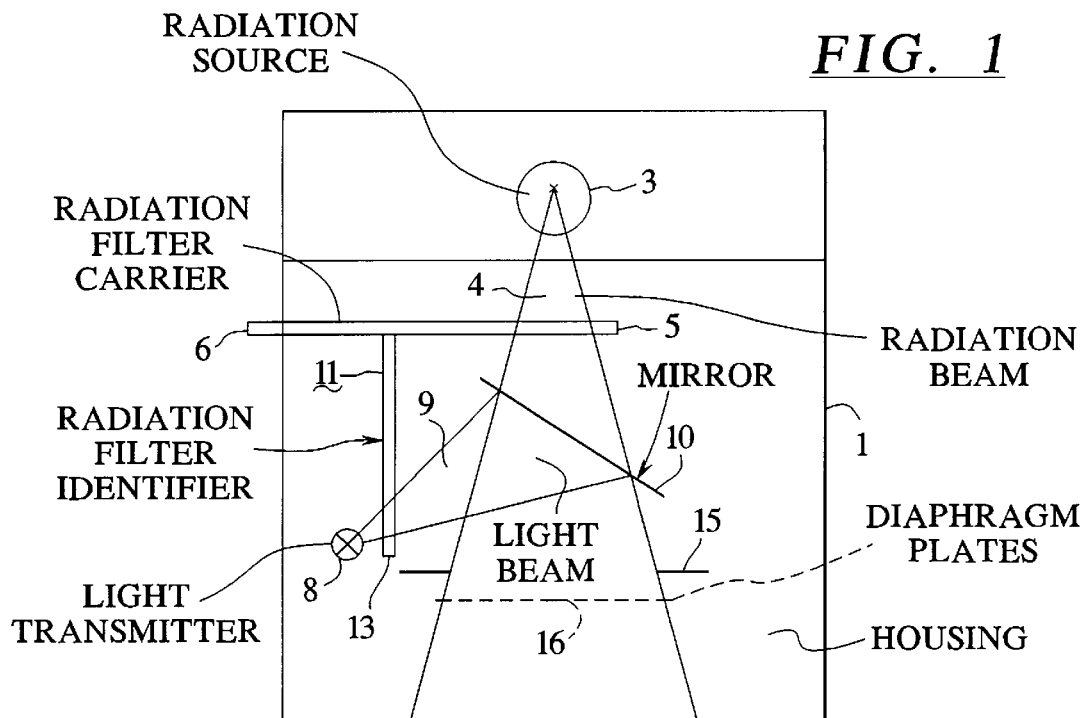
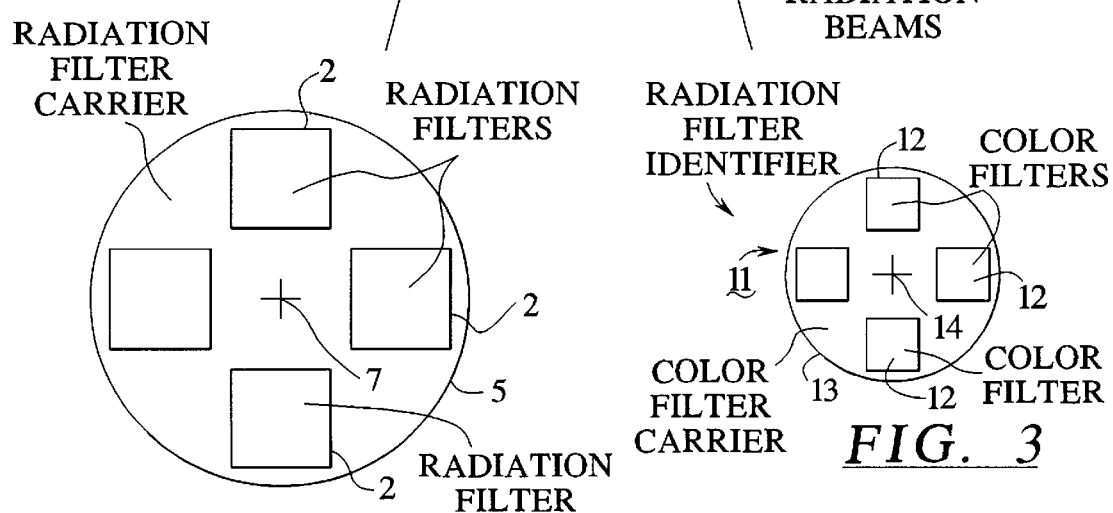
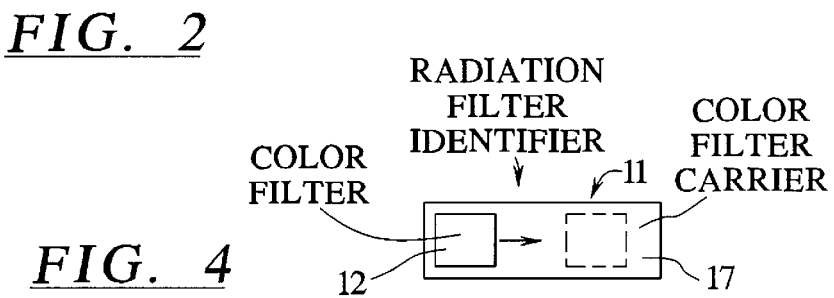

RADIATION DIAPHRAGM WITH FILTER INDICATOR

BACKGROUND OF THE INVENTION

1. Field of the Invention

The present invention is directed to a radiation diaphragm, such as a diaphragm for gating x-rays for medical diagnostic or therapy purposes, of the type wherein at least one radiation filter can be introduced into the radiation beam path.

2. Description of the Prior Art

Radiation diaphragms of the above type have a housing allocated to a radiation transmitter, the housing containing means for introducing at least one radiation filter into the beam path of a radiation bundle emanating from the radiation transmitter. The radiation filter (or filters) can be brought into the beam path or removed therefrom by means of adjusting means arranged outside the housing. It can thus be recognized only on one side of the housing whether a radiation filter is located in the beam path, and if so, which filter. The housing also contains a light transmitter for emitting a light beam emanating from the diaphragm. This light beam is directed, via a mirror which can be tilted into the light beam path, onto the subject to be treated or examined with x-rays so as to optically represent the extent of the radiation beam. This light transmitting means is known as a light sight and serves to orient the radiation transmitter onto the examination subject as well as to optically represent the region on the examination subject on which the radiation beam is incident.

In the housing, adjustable diaphragm plate pairs can be provided by which the radiation bundle can be gated in desired fashion.

Particularly in the rush which is typical in surgical or orthopedic out-patient treatment, faulty illuminations of a registered x-ray may occur, if there is a wrong filter or no filter at all in the beam path, and this is not recognized.

SUMMARY OF THE INVENTION

It is an object of the present invention to provide a radiation diaphragm of the abovementioned type, such that it is clearly evident to the operator whether there is a radiation filter in the beam path, and if so, which filter.

The above object is achieved in accordance with the principles of the present invention in a radiation diaphragm having a housing through which the radiation beam passes and means in the housing for introducing at least one radiation filter into the path of the radiation, a light transmitter which emits a light beam which optically represents the radiation beam, and means for changing the color of the light beam dependent on whether a radiation filter is disposed in the radiation beam path.

It is an advantage of the invention, that a physician or technician can easily and immediately recognize, regardless of his or her orientation relative to the diaphragm housing, whether a filter is disposed in the radiation beam path because the color of the light beam is changed dependent on whether there is a radiation filter in the radiation beam path. It is appropriate for varying colors to be allocated to respective radiation filters which have different filtering characteristics, so that a direct determination of the radiation filter utilized can be made on the basis of the color of the light beam striking the examination region.

DESCRIPTION OF THE DRAWINGS

FIG. 1 shows an exemplary embodiment of a radiation diaphragm according to the invention.

FIG. 2 shows a carrier for radiation filters suitable for use in the inventive radiation diaphragm.

FIG. 3 shows a carrier for color filters suitable for use in the inventive radiation diaphragm.

FIG. 4 shows a further exemplary embodiment for a carrier for a radiation filter or color filter suitable for use in the inventive radiation diaphragm.

DESCRIPTION OF THE PREFERRED EMBODIMENTS

FIG. 1 shows a radiation diaphragm according to the invention. The radiation diaphragm has a housing 1 containing an arrangement for the introduction of at least one radiation filter 2 (FIG. 2) into the beam path of a radiation bundle 4 emanating form a radiation transmitter 3. The arrangement for introducing the radiation filter 2 can be constructed as carrier, particularly as a disk 5, on which a number of radiation filters 2 are provided (FIG. 2). This disk 5 can be rotated around a central axis 7 via an operational control 6 arranged outside the housing 1, so that different radiation filters 2 can be introduced into the path of the radiation bundle 4. The radiation diaphragm, as is known, can contain plates 15 and 16, or an iris arrangement, for gating the x-ray beam to give it a selected size and shape. Even in the absence of such a gating arrangement, however, the size of the x-ray beam incident on a subject will vary simply dependent on the distance between the x-ray beam focus and the subject.

The radiation diaphragm thus also contains a light transmitter 8 which transmits a light bundle 9 which, for example, after being deflected via a mirror 10, emerges from the housing 1 of the diaphragm, and which, for example, optically represents the radiation beam 4 incident on an examination subject. A filter identifier 11 is inventively provided for changing the color of the light bundle 9 dependent on whether or not there is a radiation filter 2 in the beam path. If a number of various radiation filters 2 can be introduced into the beam path of the radiation bundle 4, then it is advantageous if different colors of light are respectively allocated to the radiation filters 2.

In an exemplary embodiment, the color of the light beam 9 is changed, by introducing a color filter 12 (FIG. 3) into the path of the light beam 9. To this end, the color filter 12 according to FIG. 3 can be arranged on another disk 13 which is rotatable around its central axis 14. The filter disk 5 and the filter identifier disk 13 are preferably, though not necessarily, mechanically coupled, so that, for example, the color red is allocated to a copper filter of a thickness of 0.1 mm, the color green is allocated to a copper filter of 0.2 mm thickness, and the color blue is allocated to a copper filter of 0.33 mm thickness. If no such radiation filter 2 is located in the beam path, then no color filter is allocated to the light beam 9.

In accordance with the invention, not only can the disks 5 and 13 be constructed as annular disks, but alternatively the filters can be provided side by side on a longitudinally extended carrier 17 (FIG. 4). A mechanical coupling of the disks 5 and 13 is likewise not essential. By providing electromechanical drives, an electromechanical coupling can also be employed.

Although modifications and changes may be suggested by those skilled in the art, it is the intention of the inventor to embody within the patent warranted hereon all changes and modifications as reasonably and properly come within the scope of his contribution to the art.

I claim as my invention:

1. A radiation diaphragm for use with a radiation source which emits a radiation beam propagating in a radiation beam path, said radiation diaphragm comprising:

means for introducing at least one radiation filter into said radiation beam path;

a light transmitter which emits a light beam which optically represents said radiation beam; and means for changing a color of said light beam dependent on whether a radiation filter is disposed in said radiation beam path by said means for introducing at least one radiation filter into said radiation beam path.

2. A radiation diaphragm as claimed in claim 1 wherein said means for introducing at least one radiation filter into said radiation beam path comprises means for introducing at least two different radiation filters, one at a time, into said radiation beam path; and wherein said means for changing the color of the light beam comprises means for changing the color of the light beam from among a plurality of different colors respectively identifying said at least two differing radiation filters.

3. A radiation diaphragm as claimed in claim 1 wherein said means for changing the color of the light beam comprises means for introducing at least one color filter into said light beam.

4. A radiation diaphragm as claimed in claim 3 wherein said means for changing the color of the light beam comprises a carrier carrying said at least one color filter for moving said at least one color filter into said light beam.

5. A radiation diaphragm as claimed in claim 4 wherein said carrier comprises an annular disk.

6. A radiation diaphragm as claimed in claim 1 further comprising means for coupling said means for introducing at least one radiation filter into the radiation beam path and said means for changing the color of the light beam so that the color of the light beam is automatically changed by said means for changing the color of the light beam dependent on the radiation filter introduced into the radiation beam path by said means for introducing at least one radiation filter into the radiation beam path.

7. A radiation diaphragm as claimed in claim 6 wherein said means for coupling comprises means for mechanically coupling said means for introducing at least one radiation filter into said radiation beam path to said means for changing the color of the light beam.

8. A radiation diaphragm as claimed in claim 6 wherein said means for coupling comprises means for electromechanically coupling said means for introducing at least one radiation filter into said radiation beam path to said means for changing the color of the light beam.

9. A radiation diaphragm as claimed in claim 1 further comprising means disposed in said radiation beam path for gating said radiation beam.

\* \* \* \* \*